8/23/83                4,399,822

United States Patent [19]
Theumer

[11] 4,399,822
[45] Aug. 23, 1983

[54] ULTRASONIC EQUIPMENT FOR GENERATING SECTION IMAGES

[75] Inventor: Christoph Theumer, Timelkam, Austria

[73] Assignee: Kretztechnik Gesellschaft mbH, Zipf, Austria

[21] Appl. No.: 227,479

[22] Filed: Jan. 22, 1981

[30] Foreign Application Priority Data

Jan. 23, 1980 [AT] Austria .................................. 341/80

[51] Int. Cl.[3] ............................................. A61B 10/00
[52] U.S. Cl. ...................................... 128/660; 73/633
[58] Field of Search ............................... 128/660–661; 73/618, 620, 633

[56] References Cited

U.S. PATENT DOCUMENTS

| | | |
|---|---|---|
| 4,106,492 | 8/1978 | Schuette et al. |
| 4,120,291 | 10/1978 | Paton et al. ......................... 73/618 X |
| 4,151,834 | 5/1979 | Sato et al. |
| 4,215,585 | 8/1980 | Kunii et al. ........................... 73/633 |
| 4,282,879 | 8/1981 | Kunii et al. ........................... 128/660 |
| 4,317,370 | 3/1982 | Glenn ................................ 128/660 X |

FOREIGN PATENT DOCUMENTS

712754  1/1980  U.S.S.R. ................................. 73/633

*Primary Examiner*—Lee S. Cohen
*Assistant Examiner*—Francis J. Jaworski
*Attorney, Agent, or Firm*—Kurt Kelman

[57] ABSTRACT

In ultrasonic equipment for generating section images, wherein a sector of a section surface is scanned, the angle of swing of the sound head carrier and the angular width of the sector-shaped section image can be adjusted to different values by adjusting means. For this purpose a crank mechanism is provided, which comprises a connecting rod, which is pivoted on an axis spaced from the geometric axis of rotation of the motor. The connecting rod is mounted in a bearing member, which is disposed adjacent to the axis of rotation and which is pivoted to the sound transducer head carrier on a transverse axis. The adjusted angle between the axis of the connecting rod and the axis of rotation of the motor and the angle of swing of the sound transducer head carrier can be adjusted by an alteration of the ratio of the effective length of the connecting rod to the distance from the axis of the motor to that end of the connecting rod that is nearer to the motor (FIG. 1).

4 Claims, 4 Drawing Figures

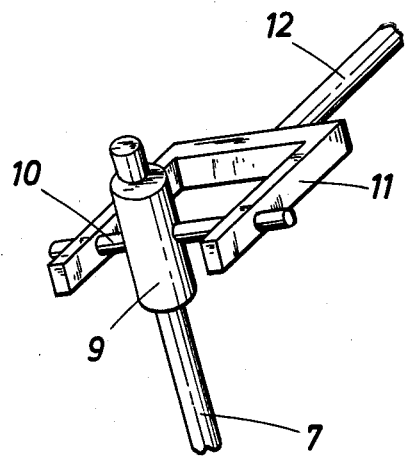
FIG.2
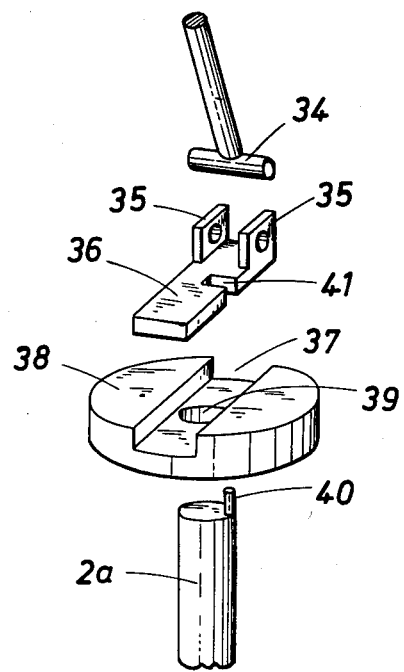

ULTRASONIC EQUIPMENT FOR GENERATING SECTION IMAGES

This invention relates to ultrasonic equipment for generating section images, comprising a scanning mechanism for scanning a sector of a section surface of an object with a sound beam which is transmitted by at least one sound transducer head, which is fixed to a sound transducer head carrier that is adapted to be driven to oscillate by a motor through the intermediary of a transmission, wherein the angle of swing of the sound transducer head carrier and the angular width of the sector-shaped section image can be adjusted to different values by adjusting means and echo signals derived from echoes generated in response to the transmitted sound pulses are adapted to be displayed on a fluorescent screen at locations which under control of position information delivered particularly by the scanning mechanism are geometrically coordinated with the locations at which said echoes have originated.

In ultrasonic equipment of that kind for generating section images, the sound transducer head or heads is or are arranged for a direct transmission of the sound beam into the object to be examined, i.e., in medical examinations into certain portions of a human body. If the sound transducer head and the sound transducer head carrier oscillate about a pivotal axis which extends substantially through the emitting surface of the sound transducer head, the section surface will be scanned in a basically triangular sector. If the pivotal axis is spaced from the sound transducer head and from the object being examined, the section surface will be scanned in a basically trapezoidal area. In the simplest case, the position information used to control the display of the section image by deflecting the baseline on the fluorescent screen is delivered by the scanning mechanism and generated in most cases by a moving element of that mechanism. But it is also known to move the baseline in dependence on time and to synchronize the sweep generator for that time-base deflection with the actual frequency of oscillation of the sound transducer head. It is also known to store the signals delivered by the sound transducer head in a buffer memory so that a flicker-free image is generated because the frequency at which the contents of the memory is read for the display exceeds the frequency at which the signals delivered from the sound transducer head are written into the memory. The use of a buffer memory affords the additional advantage that the several data can be written into the memory locations in a sequency which may differ from the sequency in which they are read. This will permit, inter alia, a writing of the signals derived from the received echoes into the memory in the sequency in which they have been received and a reading of said signals in accordance with the conventional television standard so that a television monitor can be used for the display on the fluorescent screen.

It is known from U.S. Pat. No. 4,151,834 that a sector-shaped section image having a constant angular width can be generated in that the sound transducer head carrier is driven to oscillate by a motor through the intermediary of a crank mechanism. The motor rotates only in one sense and the angular width of the section image is basically constant, as has been mentioned. Crank mechanisms of that kind have basically the disadvantage that the time patterns of the forward and backward swings of the sound transducer head carrier slightly differ from each other because there is a backlash in the crank mechanism. Owing to these differences between the time patterns, the image may be blurred or only the scanning in one direction of movement may be usable for the display of the image.

In equipment of the kind described first hereinbefore, in which the angle of the pivotal movement of the sound transducer head carrier and the angular width of the sector-shaped section image can be adjusted to different values. An extremely expensive drive mechanism of that kind is used in accordance with U.S. Pat. No. 4,106,492 and includes a motor which has an oscillating armature and through the intermediary of a speed-reducing transmission containing of a pinion and a gear segment drives the sound transducer head carrier. An additional generator is used to generate a supply voltage which has a basically sawtooth-shaped waveform and is applied to that motor having an oscillating armature. The length of each ramp of the sawtooth-shaped voltage waveform can be adjusted by adjusting means, which in this way adjust the angle through which the motor rotates and the angle of swing of the sound transducer head carrier. A control voltage for deflecting the baseline of the fluorescent screen can be derived from that supply voltage. But as the angular movement and the scanning frequency increase, the inherently desired linear movement can no longer be obtained and a sinusoidal motion is obtained in practice. This means that the speed is changed according to a sinusoidal pattern. Corrections in the generation of the supply current and in the generation of the image are required in order to obtain a more uniform motion. Besides, vibrations due to the reversal of motion cannot be avoided in practice. Whereas great advantages are afforded by a change of the angular width and of the frequency of oscillation, the known equipment of that kind can be used only in special cases owing to the difficulties arising. The main advantages afforded by a change of the angle of swing and of the frequency of oscillation reside in that a large angle of swing will permit, i.a., a cursory examination of a desired region in a body. In that case the scanning mechanism can be so adjusted, e.g., that the central portion of the scanned region is a particularly interesting area, which is then examined with a smaller angular field. As the number of sound pulses transmitted during one swing will be constant in most cases, a higher lateral resolution will be obtained if a smaller swing angle is used and a given number of pulses are transmitted during each swing. In that case, a higher depth of penetration of the sound pulses can be utilized. It may also be possible to use a smaller angle of swing and to increase the scanning rate, i.e., the frequency of oscillation. In that case, motions can be displayed more distinctly in the section image having a smaller angular width.

It is an object of the invention to provide ultrasonic equipment for generating section images which is of the kind described first hereinbefore and comprises simple means for altering the angular width of the sector-shaped section image and, if desired, permits a change of additional parameters, particularly the frequency of oscillation and depth of penetration, and which nevertheless permits the use of a simple drive mechanism, which is reliable in operation, and of a simple control device.

This object is accomplished according to the invention in that the transmission of the scanning mechanism consists of a crank mechanism for transforming the rotation of the drive motor into an oscillating motion of the sound transducer head carrier, that the crank mechanism comprises a connecting rod, which is pivoted to an eccentric disc or a crank arm on an axis that is spaced from the axis of rotation of the motor or of an interposed transmission and which adjacent to said axis of rotation is rotatably mounted in a bearing member, which is pivoted to the sound transducer head carrier on a transverse axis, that the angular movement of the sound transducer head carrier about its pivotal axis, which intersects said axis of rotation, corresponds to the included angle of the surface of an imaginary cone described by the connecting rod, and that that angular movement, which determines the transmission ratio of the crank mechanism, can be adjusted by adjusting means for altering the ratio of the effective length of the connecting rod to the distance from said axis of rotation to the point at which the connecting rod engages the eccentric disc or the crank arm.

The transmission differs from a known crank mechanism in that there is no hysteresis between the forward and reverse swings of the sound transducer head carrier. The angle of swing can be changed by simple means even when the scanning mechanism has been mounted.

According to a preferred further feature, a reversible motor is provided and the transmission is adapted to be adjusted to two different transmission ratios in dependence on the sense of rotation. A simple motor may be used in that case.

In a practical version of the last-mentioned embodiment, the eccentric disc is rotatably mounted on the motor shaft, the connecting rod is mounted in a slider, which is adjustable in the eccentric disc particularly in a diametral direction and which by coupling means carried by the motor shaft is adjustable to one or the other of two positions in dependence on the sense of rotation of the motor shaft, and which in said positions holds the point where the connecting rod engages the eccentric disc at different distances from the axis of the motor shaft, and the coupling means are arranged to transmit the rotation of the motor to the eccentric disc by means of the slider when the latter is in either of said two positions. Besides, the adjusting means may be used to positively adjust the frequency of oscillation so that it increases in response to a decrease of the angle of swing. This may be effected by the use of a motor which is controlled to rotate at a higher speed in one sense of rotation than in the other.

It has already been mentioned that each point of the image on the fluorescent screen must necessarily be coordinated with the location at which the echo has originated from which the echo signal generating the point of the image has been derived. A correct coordination has necessarily the result that an alteration of the scanning angle will result in an alteration of the angular width of the sector-shaped image. In order to prevent the non-uniform motion of the sound head from resulting in a non-uniform lateral resolution, a trigger pulse generator may be provided, which generates trigger pulses for triggering the generation of the sound pulses and by said trigger pulse controls the repetition frequency of the sound pulses in dependence on the extent of the movement performed by the sound transducer head and said trigger pulse generator is adapted to be operated by the sound transducer head carrier and its drive shaft and causes the sound pulses to be triggered whenever the sound transducer head carrier has traversed a predetermined angle. The trigger pulse generator may be controlled to produce pulses in a number which is a multiple of the sound pulses to be transmitted and a selector may be provided, which is coupled to the means for adjusting the swing angle and selects the desired pulses for triggering the desired sound pulses from the pulses delivered by the trigger pulse generator.

A buffer memory may be provided, which serves to store the signals derived from the echo pulses which have been received and which is adapted to be interrogated for the display on the fluorescent screen at a rate and/or in a sequency which differs from the writing rate or sequence.

The invention is illustrated by way of example on the accompanying drawing, in which:

FIG. 1 is a highly diagrammatic view showing ultrasonic equipment according to the invention for generating section images. The essential parts of the scanning mechanism have been shown in a simplified form in perspective. The remaining parts have been shown in a block circuit diagram.

FIG. 2 is a perspective and partly exploded view that part of the mechanism which permits an alteration of the transmission ratio.

Figure 1:
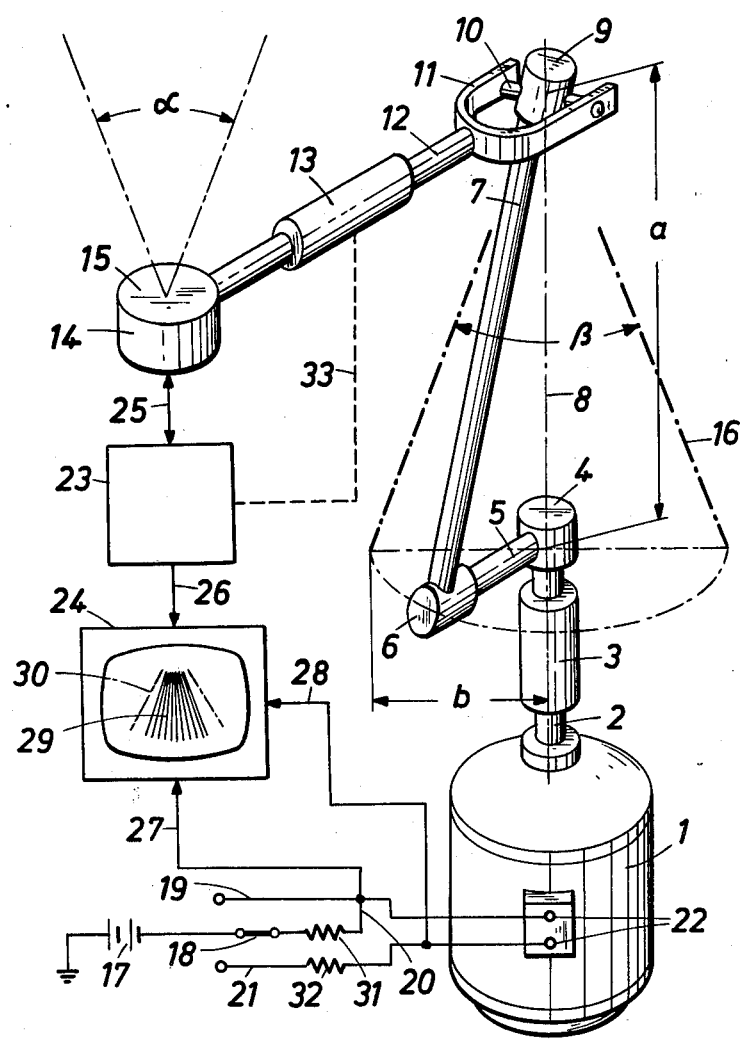

FIG. 1 shows a motor 1 having a shaft 2 which is mounted in a bearing 3. A head 4 is mounted on the shaft 2 and carries a crank arm 5, to which a connecting rod 7 is pivoted by means of an articulated joint 6 comprised of bearing member, yoke 6' and transverse axle 6'' pivoting the yoke to the bearing member. Adjacent to the axis of rotation 8 of the motor, that connecting rod 7 extends into a bearing member 9, which like a gimbal mount is pivoted in a yoke 11 on a transverse axis 10. The yoke 11 is rigidly connected to a shaft 12. The shaft 12 is mounted in a stationary bearing member 13 and is adapted to be oscillated about the axis of the bearing member 13. The shaft 12 carries a sound transducer head carrier 14, to which a sound transducer head 15 is fixed. The axis 8 and the axis of the shaft 12 include a right angle. This arrangement is not absolutely necessary but assumed because it facilitates the subsequent explanation of the geometrical relationships. It is essential that the transverse axis 10 intersects the axis 8. If the axis of the shaft 12 lies in the sound-emitting surface 15 of the sound transducer head 15, the latter will merely oscillate about the axis of the shaft 12 so that an object to which the sound transducer head has been applied will be scanned by the sound beam transmitted by the sound transducer head in a section surface which has basically the configuration of a triangle or, more precisely, a sector of a circle. If the emitting surface of the sound transducer head 15 is spaced from the axis of the shaft 12, that emitting surface will oscillate about the axis of the shaft 12 and will scan a section surface which is basically trapezoidal. The entire scanning mechanism as well as the sound transducer head 15 and the motor 1 are enclosed in a housing that serves as a handle or is provided with a handle. If required, the housing may have adjacent to the sound transducer head 15 a sound exit window provided with a sound-permeable diaphragm or the like. The subsequent explanation will be based on the assumption that the axis of the shaft 12 lies in the sound-emitting surface of the sound transducer head 15. Owing to the arrangement of the articulated joints 6, 6', 6'' and 9, 10, 11, the connecting rod 16 describes on the surface 16 of an imaginary cone in response to a rotation of the motor. Because the shaft 12 can rotate only about the axis of the stationary bearing member 13, the gyratory motion of the connecting rod 7 will be transmitted to the shaft 12 only as far as that component of motion is concerned which has the same direction as the transverse axis 10. As a result, an oscillation about the axis of the bearing member 13 is imparted to the shaft 12 and the sound transducer head 15. The angle of swing α of the sound transducer head 15 or of its carrier corresponds to the included angle β of the imaginary cone 16 described by the connecting rod 7. If the angular velocity of the shaft 2 is designated ω, the resulting relationship can be expressed as follows:

$$\alpha = \arctan\left(\frac{b}{a} \times \sin\left(\omega \times t\right)\right)$$

The frequency of oscillation of the sound transducer head 15 corresponds to the frequency of rotation of the shaft 2. The time pattern of the pivotal motion is independent from the sense of rotation of the motor because the function described is perfectly symmetrical. The maximum angle of swing of the sound transducer head 15 depends on the ratio of the effective length a of the connecting rod 7 to the effective length b of the distance from the axis 8 to the point where the connecting rod 7 engages the crank arm 5. For this reason the angle of swing α can be altered by an alteration of a and/or b. This will be permitted in the embodiment of FIG. 1 if the bearing member 6 is slidable on the crank arm 5 or the bearing member 9 is slidable on the connecting rod 7. The corresponding alteration of the effective lengths a and b may be effected by means of magnets or other adjusting means or, as far as the length a is concerned, by an axial shifting of the motor, which in that case is longitudinally slidably mounted, so that the rod 7 will be longitudinally shifted relative to the slidable bearing member 9. The design which will now be described permits a change of the ratio of a to be simply by a change of the sense of rotation.

It is assumed that the motor 1 shown in FIG. 1 is a reversible and speed-variable motor. A power source 17 for feeding the motor 1 is connected to a switch 18, which has three control positions and, if desired, an open position, and in said control positions connects the power source 17 via respective leads 19, 20, 21 to either of the two input terminals 22 of the motor 1. Lead 21 is connected to the input terminal that is associated with one sense of rotation. Leads 19 and 20 are connected to the other input terminal. It has been mentioned hereinbefore that in response to a reversal of the motor the angle of swing α is to be altered from one predetermined value to another in that the ratio a:b is altered in a manner to be described hereinafter. It is assumed that the larger angle of swing is to be obtained when the sense of rotation is controlled by the energization of the motor via lead 21 and the smaller angle of swing is to be obtained when the sense of rotation is controlled by the energization of the motor via lead 20 or 21. In response to an energization via leads 20, 21, the motor 1 rotates at the same speed but in different senses. When the motor is energized via lead 19, the motor will operate at a higher speed so that the frequency of oscillation and the picture frequency of the section image will be increased.

The entire section display equipment will now be explained with reference to the simplified block circuit diagram, in which block 23 represents the entire control and evaluation electronics and a display unit comprising a fluorescent screen is designated 24. The unit 23 includes a clock, a control pulse generator for operating the sound transducer head, a receiver, an amplifier, an echo signal demodulator and deflection and unblanking control means for controlling the image on the fluorescent screen of unit 24. Only a lead 25 connected to the sound transducer head and a lead 26 connected to the display unit 24 have been indicated. Additional data indicating the selected sense of rotation or speed of the motor and synchronizing pulses can be delivered to the control unit 23 or the display unit 24 via leads 27, 28. Corresponding data may be derived from sensors provided at different parts of the mechanism and may be delivered to the unit 23 or the display unit 24. The echo signals obtained as a result of the scanning of a section surface with the sound beam are used to generate on the fluorescent screen of the display unit 24 a section image. The echo signals may be used directly to generate the section image or may be stored in a buffer memory and subsequently read from said memory for the display on the fluorescent screen. In either case, the section image 29 on the fluorescent screen of unit 24 will represent the smaller of the possible fields and will have a higher lateral resolution when the switch 18 is in the position shown. When the switch 18 is moved to the position for energizing the motor via the lead 19, the speed of the motor and the frequency of oscillation of the sound transducer head 15 will be increased. As a result, the resolution with respect to time will be improved and the lateral resolution will be reduced in comparison to the case described last hereinbefore. If the switch 18 causes the motor to be energized via lead 21, the angular field of the image on the fluorescent screen will be increased as far as to the limits designated 30 and the angle α will be increased too.

To ensure that a uniform lateral resolution will be obtained in spite of the non-uniform pivotal movement, a sensor, which may be accommodated, e.g., in the bearing member 13, may be used to generate trigger pulses which are derived from the motion of the shaft 12 and of the sound transducer head 15 and which trigger the control pulse generator that is accommodated in the unit 23. In this way, a pulse can be emitted whenever a certain angle has been traversed.

Resistors 31, 32 have been shown to be included in leads 20, 21 in order to indicate that the energization of the motor via lead 19 will result in a different speed than the energization of the motor via lead 20 or 21. The sensor in the bearing member 13 may respond to a reversal by a delivery of trigger signals to the function generator 23 so that the deflection of the baseline on the fluorescent screen of unit 24 will be positively synchronized with the pivotal movement of the sound transducer head. For this purpose, a lead 33 connects the sensor accommodated in the bearing member 13 to the control section of the equipment. The pulse repetition frequency can be altered by means of additional switches, not shown.

It is apparent from the upper portion of FIG. 2 that the connecting rod 7 can be shifted in the bearing in order to alter the distance a. The design shown in FIG. 1 has been modified in that a transverse pivot 34 is connected to the lower end of the connecting rod 7 and is used to pivot the connecting rod in a bearing eyes 35 of a slider 36. The slider 36 is mounted in a diametral groove 37 formed in an eccentric disc 38 and is slidable along said groove. The motor shaft 2a is rotatably mounted in a bore 39 of the eccentric disc 38 and carries a coupling pin 40, which extends into a transverse slot 41 of the slider 36. The diameter of the bore 39 is smaller than the width of the groove 37. The pin 40 is eccentrically mounted at the end of the shaft 2a. The coupling pin 40 always protrudes into the slot 41. The eccentric disc 38 may constitute a flywheel.

Figure 3:
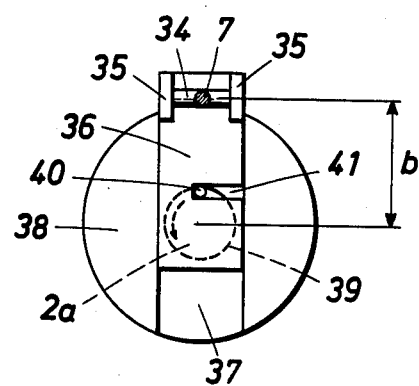
FIGS. 3 and 4 are top plan views showing the eccentric disc of the mechanism in two possible adjusted positions.
Figure 4:
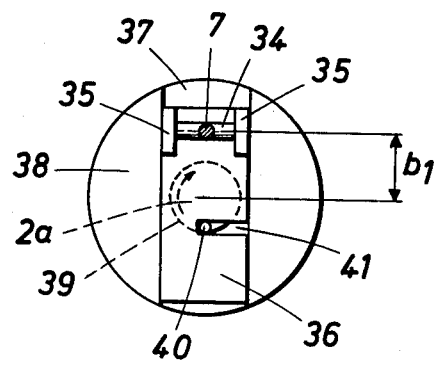

During a rotation in the sense indicated in FIG. 3, the slider 36 is in the position shown and the axis of shaft 2a is spaced by the distance b from the axis of the pivot 34 where the connecting rod 7 engages the eccentric member consisting of the eccentric disc 38 and the slider 36. When the sense of rotation is reversed, the coupling pin 40 shifts the slider 36 in the groove 37 to the position shown in FIG. 4 and only thereafter rotates the crankshaft 38 by means of the slider 36. The distance from the axis of the shaft 2a to the point of engagement 34 of the connecting rod 7 is then decreased to $b_1$. The coupling is ensured in that the pin 40 engages the end of the slot. As a result of the change from b to $b_1$, the angle of swing will also be proportionally decreased. If it is desired to use three different angles of swing, detent means may be provided to holding the slider 36 in a position which is intermediate the positions of FIGS. 3 and 4 so that the slider can be moved from the position shown in FIG. 2 until it is arrested by the detent means. This position corresponds to a third angle of swing. Only when the detent means have been released, can the slider be moved to the position shown in FIG. 4. That release can be magnetically effected in most cases.

What is claimed is:

1. In ultrasonic equipment for examinations using section displays, comprising
   a pivoted carrier,
   sound transducer head means carried by, and fixed to, said carrier and operable to transmit an ultrasonic sound beam into a section surface of an object to be examined and to derive echo signals from echoes orignated in said section surface in response to said sound beam,
   a scanning mechanism including a rotary reversible motor and a transmission operable by said motor to impart to said carrier an oscillating pivotal motion through an angle of swing whereby said sound beam is caused to scan a sector of said section surface, said transmission consisting of a crank mechanism for transforming a rotational motion of said motor into said oscillating angular motion and comprises an eccentric member adapted to be rotated by said motor about an axis of rotation, a connecting rod pivoted to said eccentric member on a first pivotal axis spaced from said axis of rotation, and a bearing member disposed adjacent to said axis of rotation and pivoted to said carrier on a second pivotal axis which is transverse to said axis of rotation, said connecting rod being rotatably mounted in said bearing member, said carrier being pivoted on a third pivotal axis which intersects said axis of rotation, and said connecting rod being arranged so that, in response to a rotation of said eccentric member about said axis of rotation, said connecting rod describes a surface of an imaginary cone having an included angle that is equal to said angle of swing and imparts to said carrier a pivotal movement about said third pivotal axis through said angle of swing,
   a display unit comprising a fluorescent screen,
   display control means for causing said display unit to display on said fluorescent screen a section image in which each of said echo signals is displayed at a location which is geometrically coordinated with the location at which the corresponding echo has originated in said section surface, and
   adjusting means for adjusting said angle of swing and the angular width of said section image, said adjusting means being adapted to alter the ratio of the effective length of said connecting rod between said first and second pivotal axes to the distance from said axis of rotation to said first pivotal axis, whereby said angle of swing is altered as well as the transmission ratio of said crank mechanism, said adjusting means being arranged to adjust said ratio to a first value in response to an initiation of a rotation of said motor in a first sense and to adjust said ratio to a second value in response to an initiation of a rotation of said motor in a second sense.

2. The improvement set forth in claim 1, wherein
   said motor has an output shaft centered on said axis of rotation,
   said eccentric member consists of an eccentric disc rotatably mounted on said output shaft,
   said adjusting means comprise a slider adjustably slidably mounted in said eccentric disc and coupling means carried by said output shaft and arranged to move said slider relative to said eccentric disc to a first position in response to an initiation of a rotation of said output shaft in a first sense and to a second position in response to an initiation of a rotation of said output shaft in a second sense and to transmit the rotation of said output shaft to said eccentric disc when said slider is in either of said first and second positions,
   said connecting rod is pivoted to said slider on said first pivotal axis, and
   said first pivotal axis is spaced different distances from said axis of rotation when said slider is in said first and second positions.

3. The improvement set forth in claim 2, wherein said slider is diametrically movable relative to said eccentric disc.

4. The improvement set forth in claim 1, wherein said scanning mechanism is arranged to reduce the frequency of oscillation of said oscillating angular motion in response to a decrease of said angle of swing.

* * * * *